(12) United States Patent
Borgman et al.

(10) Patent No.: US 8,258,164 B2
(45) Date of Patent: Sep. 4, 2012

(54) NITROIMIDAZOLE COMPOSITION AND METHOD

(75) Inventors: Robert J. Borgman, Mundelein, IL (US); James E. Juul, Wauconda, IL (US)

(73) Assignee: Curatek Pharmaceuticals Holding, Inc., Elk Grove Village, IL (US)

( * ) Notice: Subject to any disclaimer, the term of this patent is extended or adjusted under 35 U.S.C. 154(b) by 1516 days.

(21) Appl. No.: 11/519,326

(22) Filed: Sep. 12, 2006

(65) Prior Publication Data

US 2008/0063670 A1    Mar. 13, 2008

(51) Int. Cl.
*A01N 43/50* (2006.01)
*A61K 31/415* (2006.01)

(52) U.S. Cl. ........ 514/398; 424/1.25; 424/433; 435/142

(58) Field of Classification Search ................ 514/398, 514/396; 424/1.25, 433; 435/142
See application file for complete search history.

(56) References Cited

U.S. PATENT DOCUMENTS

| | | | | |
|---|---|---|---|---|
| 4,837,378 A | * | 6/1989 | Borgman | 514/398 |
| 4,861,580 A | * | 8/1989 | Janoff et al. | 424/1.21 |
| 5,536,743 A | * | 7/1996 | Borgman | 514/398 |
| 6,348,203 B1 | * | 2/2002 | Goodman et al. | 424/401 |

FOREIGN PATENT DOCUMENTS

GB    2000025 A  *  1/1979

OTHER PUBLICATIONS

Cornejo-Bravo, J., Kinetics of Drug Release from Hydrophobic Polybasic gels: Effects of Buffer Acidity, Journal of Controlled Release 33 (1995) 223-229.*
Fischer, M., On the Liquefaction or Solution of Gelatin in Polybasic Acids and their Salts, University of Cincinnati (1917) 303-312.*
Wang, M., Effect of Polybasic Acids on Structure of Aluminum Hydroxycarbonate Gel, Journal of Pharmaceutical Sciences (1980) 668-671.*

* cited by examiner

*Primary Examiner* — Fereydoun G Sajjadi
*Assistant Examiner* — Danielle Sullivan
(74) *Attorney, Agent, or Firm* — Olson & Cepuritis, Ltd.

(57) ABSTRACT

An aqueous nitroimidazole composition comprises metronidazole, tinidazole or a combination thereof at a concentration greater than the solubility of the free base form of the nitroimidazole in water at 20° C., and a nitroimidazole crystallization-inhibiting amount of at least one organic acid. The organic acid preferably is a lower alkyl carboxylic acid (e.g., acetic acid), a polybasic acid (e.g., citric acid, tartaric acid, malic acid, polyacrylic acid, and the like), or a combination thereof. The composition can further include a thickening agent, to form a gel. The composition is free from organic co-solvents, water-soluble vitamins, and cyclodextrins; and free from nitroimidazole crystals at an ambient temperature of about 20° C. Methods of preparing the composition are also described.

27 Claims, No Drawings

NITROIMIDAZOLE COMPOSITION AND METHOD

FIELD OF THE INVENTION

The invention relates generally to compositions comprising a nitroimidazole, such as metronidazole or tinidazole. More particularly, the invention relates to aqueous compositions of metronidazole and/or tinidazole, as well as methods of preparing said compositions.

BACKGROUND OF THE INVENTION

Metronidazole (1-(2-hydroxyethyl)-2-methyl-5-nitroimidazole) and tinidazole (1-[2-(ethylsulfonyl)ethyl]-2-methyl-5-nitroimidazole) are synthetic nitroimidazole antimicrobial agents, which have been useful for the treatment of bacterial vaginosis (BV) and vaginal trichomoniasis. Both compounds exhibit activity against *Trichomonas vaginalis, Giardia duodenalis*, and *Entamoeba histolytica* protozoa and are also active against bacterial vaginosis pathogens such as *Bacteriodes* species, *Peptostreptococcus* and other anaerobes. In addition, metronidazole has been used in the treatment of rosacea, acne and other inflammatory skin conditions. Nitroimidazoles have been used to treat a variety of conditions including vaginal disorders and protozoal disorders.

U.S. Pat. No. 5,536,743 to Borgman describes a pH buffered, aqueous gel formulation of the antimicrobial agent metronidazole for treatment of bacterial vaginosis. Metronidazole has very limited solubility in water (less than about 1 percent by weight in water at neutral pH), so compositions containing metronidazole at concentrations of about 1 percent by weight or greater, generally include insoluble metronidazole crystals or must include organic co-solvents, cyclodextrins or water-soluble vitamins to aid in the solubilization of the metronidazole.

Tinidazole has a similarly limited solubility in water (about 0.45 percent by weight at neutral pH). It is difficult to obtain stable, physiologically-acceptable aqueous tinidazole solutions at concentrations above about 0.45 percent by weight, which are free from tinidazole crystals.

There is an ongoing need for aqueous nitroimidazole solutions that include a greater concentration of nitroimidazole (e.g., metronidazole and/or tinidazole) than the solubility limit in neutral water, which are free from organic co-solvents, water-soluble vitamins, and cyclodextrins, and free from undissolved nitroimidazole crystals. The present invention provides such aqueous nitroimidazole compositions.

SUMMARY OF THE INVENTION

An aqueous nitroimidazole composition of the invention comprises a nitroimidazole (i.e., metronidazole, tinidazole, or a combination thereof) at a concentration higher than the solubility of the nitroimidazole free base in deionized water at about 20° C., and a nitroimidazole crystallization-inhibiting amount of at least one organic acid, such as a lower alkyl carboxylic acid (e.g., acetic acid) or a polybasic acid (e.g., citric acid, tartaric acid, malic acid, polyacrylic acids, and the like). Preferably, the concentration of nitroimidazole in the composition is at least about 20 percent higher than the solubility of the free base form of the nitroimidazole in deionized water. The compositions are free from organic co-solvents, water-soluble vitamins, and cyclodextrins, and free from nitroimidazole crystals at an ambient temperature of about 20° C. The compositions of the present invention are useful for treating a variety of human diseases such as bacterial and protozoal infections and various dermatologic conditions such as rosacea, acne, and dermatitis.

In a preferred embodiment, the composition includes at least about 1 percent by weight of metronidazole dissolved in water, more preferably at least about 1.2 percent by weight. The at least one organic acid preferably is present in the composition in a molar amount in the range of about 50 to about 150 mole percent based on the molar amount of metronidazole dissolved in the composition.

In another preferred embodiment, the composition includes at least about 0.5 percent by weight of tinidazole dissolved in water, more preferably at least about 0.55 percent by weight. The at least one organic acid preferably is present in the composition in a molar amount in the range of about 50 to about 150 mole percent based on the molar amount of tinidazole dissolved in the composition.

Another aspect of the present invention is a nitroimidazole gel composition comprising a nitroimidazole selected from the group consisting of metronidazole, tinidazole, and a combination thereof. The composition includes an amount of the nitroimidazole greater than the solubility of the free base form of the nitroimidazole in deionized water at an ambient temperature of about 20° C., a nitroimidazole crystallization-inhibiting amount of at least one organic acid, and a thickening agent in an amount sufficient to gel the composition. Preferably, the thickening agent comprises a hydroxypropyl methylcellulose, a polyacrylic acid (e.g., a crosslinked polyacrylic acid), and the like, or a combination of two or more thickening agents. In some preferred embodiments, the composition further comprises a polyol such as propylene glycol.

A method aspect of the present invention involves preparing an aqueous solution of a nitroimidazole selected from the group consisting of metronidazole, tinidazole, and a combination thereof at a nitroimidazole concentration greater than the solubility of the nitroimidazole free base in deionized water. The method comprises dissolving the nitroimidazole in water containing a nitroimidazole crystallization-inhibiting amount of at least one organic acid and free from organic co-solvents, water-soluble vitamins, and cyclodextrins.

DETAILED DESCRIPTION OF PREFERRED EMBODIMENTS

The terms "pharmaceutically acceptable", "physiologically tolerable", "physiologically compatible", and grammatical variations thereof, as used herein and in the appended claims as they refer to electrolytes (e.g., salts), bases, diluents, preservatives, buffers and other excipients, are used interchangeably and represent that the materials are capable of topical administration to human skin and to the human vagina without the production of medically unacceptable levels of undesirable physiological effects such as irritation, itching, stinging, or systemic effects such as nausea, dizziness, and the like.

The present invention provides aqueous nitroimidazole compositions comprising metronidazole, tinidazole or a combination thereof, having a concentration of dissolved nitroimidazole that is greater than the solubility of the nitroimidazole free base in deionized water at about 20° C. The compositions are free from organic co-solvents, water-soluble vitamins, and cyclodextrins, and free from nitroimidazole crystals. In the compositions of the present invention, the nitroimidazole is solubilized by the presence of a nitroimidazole crystallization-inhibiting amount of at least one organic acid. Preferably, the concentration of nitroimidazole in the composition is at least about 20 percent greater than the solubility of the nitroimidazole free base in deionized water.

In some preferred embodiments, the compositions contain up to about 1.25 percent by weight of dissolved metronidazole. In other preferred embodiments, the compositions comprise up to about 0.6 percent by weight of tinidazole.

In some preferred embodiments, the compositions include a gelling agent in amount sufficient to form an aqueous gel. The gel compositions preferably have a pH in the range of about 3.5 to about 6.

Suitable organic acids include, without limitation, lower alkyl carboxylic acids (e.g., acetic acid), polybasic acids (e.g., citric acid; tartaric acid; malic acid; polyacrylic acids such as linear polyacrylic acid and crosslinked polyacrylic acid; and the like) and combinations thereof. A preferred organic acid is citric acid. Another preferred organic acid is tartaric acid. Preferred polyacrylic acids include CARBOPOL® thickening agents, and NOVEON® brand polycarbophil crosslinked polyacrylic acids, available from Noveon, Inc., Cleveland Ohio. A combination of two or more organic acids can be utilized to solubilize the nitroimidazole, as well.

In some preferred embodiments, the organic acid is present in the composition in at a concentration in the range of about 50 to about 150 mole percent based on the molar amount of nitroimidazole dissolved in the composition, more preferably in a molar amount about equal to the molar amount of nitroimidazole in the composition.

The compositions of the present invention optionally can include a physiologically tolerable preservative, as well as pharmaceutically acceptable excipients, so long as the optional components do not interfere with the solubility of the metronidazole.

Suitable physiologically tolerable preservatives include bacteriostats, preservatives, inhibitors, and the like, such as methyl, ethyl, propyl, and butyl esters of parahydroxybenzoic acid (parabens); propyl gallate; sorbic acid and its sodium and potassium salts; propionic acid and its calcium and sodium salts; 6-acetoxy-2,4-dimethyl-m-dioxane; 2-bromo-2-nitropropane-1,3-diol; salicylanilides such as dibromosalicylanilide and tribromosalicylamilide, the cis isomer of 1-(3-chloroallyl)-3,5,7-triaza-1-azanidadamantane chloride; hexachlorophene; sodium benzoate; chelating agents such as ethylene diaminetetraacetic acid (EDTA), citric acid, and their alkali metal salts; phenolic compounds such as butyl hydroxyanisole, butyl hydroxytoluene, chloro- and bromocresols, and the like; quaternary ammonium compounds such as benzalkonium chloride; aromatic alcohols such as 2-phenylethyl alcohol and benzyl alcohol; chlorobutanol; quinoline derivatives such as iodochlorohydroxyquinoline; and the like.

Pharmaceutically acceptable excipients that can be included in the compositions of the present invention include, for example, physiologically tolerable thickeners, surfactants, colorants, fragrances, and the like, which are well known in the art. Preferred thickeners (e.g., for forming a gel composition) include hydroxypropyl methylcellulose compounds and crosslinked polyacrylic acids.

Another aspect of the present invention is a nitroimidazole gel composition comprising a nitroimidazole selected from the group consisting of metronidazole, tinidazole, and a combination thereof. The composition includes an amount of the nitroimidazole greater than the solubility of the free base form of the nitroimidazole in deionized water at an ambient temperature of about 20° C., a nitroimidazole crystallization-inhibiting amount of at least one organic acid, and a thickening agent in an amount sufficient to gel the composition.

Preferably, the thickening agent comprises a hydroxypropyl methylcellulose, a polyacrylic acid (e.g., a crosslinked polyacrylic acid, such as a CARBOPOL® or polycarbophil-type crosslinked polyacrylic acid), and the like. The composition can also comprises a combination of two or more thickening agents.

Some preferred embodiments of gelled nitroimidazole compositions of the invention also include a polyol, such as glycerol, propylene glycol, and the like. A preferred polyol is propylene glycol.

The present invention also provides a method for preparing an aqueous composition comprising a nitroimidazole selected from the group consisting of metronidazole, tinidazole, or a combination thereof, which is free from organic co-solvents, water-soluble vitamins, and cyclodextrins, and free from metronidazole crystals at an ambient temperature of about 20° C. and which has a nitroimidazole concentration greater than the solubility of the nitroimidazole free base in deionized water at about 20° C. Preferably, the composition has a nitroimidazole concentration of at least about 20 percent higher than the solubility of the nitroimidazole free base in deionized water at an ambient temperature of about 20° C. The method comprises dissolving metronidazole, tinidazole or a combination thereof in an aqueous solution containing a nitroimidazole crystallization-inhibiting amount of at least one organic acid. In some preferred embodiments the organic acid is a lower alkyl carboxylic acid, such as acetic acid. In other preferred embodiments, the organic acid is a polybasic acid (e.g., a polybasic acid selected from the group consisting of citric acid, tartaric acid, and malic acid.

In a preferred embodiment, an amount of metronidazole is dissolved in the composition to obtain a metronidazole concentration of at least about 1 percent by weight, more preferably at least about 1.2 percent by weight. The concentration of organic acid in the solution preferably is in the range of about 50 to about 150 mole percent based on the molar amount of metronidazole in the composition. More preferably, the amount of organic acid is at least about equal to the molar amount of metronidazole dissolved in the solution.

In another preferred embodiment, an amount of tinidazole is dissolved in the composition to obtain a tinidazole concentration of at least about 0.5 percent by weight, more preferably at least about 0.55 percent by weight. The concentration of organic acid in the solution preferably is in the range of about 50 to about 150 mole percent based on the molar amount of tinidazole in the composition. More preferably, the amount of organic acid is at least about equal to the molar amount of tinidazole dissolved in the solution.

Another aspect of the present invention is an article of manufacture comprising packaging material and at least one composition of the invention in at least one sealed container within the packaging material. Preferably, the compositions are gels containing a thickening agent. The container comprises a label that includes printed indicia describing the contents, such as a listing of ingredients, the manufacturer's name and address, and the like. Preferably, the packaging material also includes a printed insert including detailed information on the composition, its method of administration for treatment of infections, side effects, contraindications, and the like indicia, which may be required by governmental agencies responsible for regulation of pharmaceutical products. The articles of manufacture may also include applicators, such as a tubular applicator that can be used in conjunction with a storage vessel or squeezable tube to aid in applying the compositions of the invention (e.g., into the vagina). In addition, the container can be a single use packet or a pre-filled applicator.

The following non-limiting examples further illustrate the present invention.

EXAMPLE 1

Solubilization of Nitroimidazoles in Water

Weighed amounts of nitroimidazoles (i.e., metronidazole and tinidazole) were added to water in separate containers, with and without acids present. Heat was applied, if necessary, to dissolve the nitroimidazole. No organic co-solvents, water-soluble vitamins, or cyclodextrins were present in the solutions. The amount of acid was selected to be about equimolar with the amount of nitroimidazole added. After the nitroimidazole was dissolved, each solution was cooled to about 4° C. to force crystallization of some of the nitroimidazole. If crystals were not observed upon cooling, seed crystals of nitroimidazole were added and the solution were again maintained at about 4° C. After crystal formation was observed in all solutions, the solutions were allowed to warm to room temperature (about 20° C.). Each solution was observed at about 20° C. over a period of about 14 days to determine if the crystals would re-dissolve. The absence of crystals after 14 days indicates effective dissolution of the nitroimidazole. Table 1 includes dissolution data for a number of compositions comprising varying amounts of metronidazole and various acids. Table 2 includes dissolution data for a number of compositions comprising varying amounts of tinidazole and various acids.

TABLE 1

| | Metronidazole Concentration | | | |
|---|---|---|---|---|
| Acid | 0.8% | 1.0% | 1.2% | 1.25% |
| None | − | + | ND | + |
| Hydrochloric | − | − | + | ND |
| Acetic | − | − | + | ND |
| Tartaric | − | − | − | ND |
| Citric | ND | − | ND | − |

− means no crystals present
+ means crystal are present
ND means experiment not performed The data in Table 1 clearly indicate that solutions having a metronidazole concentration of at least about 1 percent by weight and free from metronidazole crystals at 20° C. were obtained utilizing organic acids (e.g., acetic acid, citric acid, tartaric acid, and malic acid). Metronidazole concentrations as high as 1.25 percent by weight were obtained utilizing citric acid.

TABLE 2

| | Tinidazole Concentration | | | |
|---|---|---|---|---|
| Acid | 0.45% | 0.50% | 0.55% | 0.60% |
| None | − | + | + | + |
| Hydrochloric | − | − | − | + |
| Acetic | − | − | + | + |
| Tartaric | − | − | − | + |
| Citric | − | − | − | + |

− means no crystals present
+ means crystal are present

The data in Table 2 indicate that a solution having a tinidazole concentration as high as about 0.55 percent by weight and free from tinidazole crystals at 20° C. was obtained utilizing citric acid and using tartaric acid.

EXAMPLE 2

Gel Compositions

Various composition were made that incorporate the active compounds for use in the treatment of various diseases. Formulations with lower pH and higher viscosity will be useful for vaginal infections and those with higher pH and lower viscosity will prove useful for dermatologic conditions. Examples are shown in Table 3.

TABLE 3

| Ingredient | Percentage | TNZ 0.55% pH 4 | TNZ 0.55% pH 5.25 | MTZ 1.0% pH 4 |
|---|---|---|---|---|
| Tinidazole (TNZ) | | 0.55 g | 0.55 g | |
| Metronidazole (MTZ) | | | | 1 g |
| MethoCel K100M | 2 | 2 g | | 2 g |
| MethoCel E4A | 2-3 | | 2 g | |
| Propylene glycol | 5 | 5 g | 5 g | 5 g |
| Methyl paraben | 0.08 | 80 mg | 80 mg | 80 mg |
| Propyl paraben | 0.02 | 20 mg | 20 mg | 20 mg |
| EDTA | 0.05 | 50 mg | 50 mg | 50 mg |
| Citric acid | | 0.5 g | 0.5 g | 1.23 g |
| Sodium citrate | | 0.25 g | 1.25 g | 1.16 g |
| Water, q.s. | | to 100 g | to 100 g | to 100 g |

A polyacrylic acid-based gel composition was prepared utilizing CARBOPOL® crosslinked polyacrylic acid as the organic acid and as a gelling agent. The formulation of this polyacrylic acid-based gel is provided in Table 4. The composition was prepared by slowly adding the polyacrylic acid to about 80 grams of water until the polyacrylic acid was wetted. A separate solution containing the tinidazole, propylene glycol, methyl paraben, propyl paraben, and EDTA was prepared by mixing these components in about 100 grams of water. The solution and the wetted polyacrylic acid were then mixed together and the sodium hydroxide was added to form a gel having a pH of about 5.3. The resulting polyacrylic acid based gel was clear and free from tinidazole.

TABLE 4

| Ingredient | Percentage | Weight |
|---|---|---|
| Tinidazole (TNZ) | 0.5 | 1 g |
| CARBOPOL ® polyacrylic acid | 2 | 4 g |
| Propylene glycol | 5 | 6 g |
| Methyl paraben | 0.08 | 160 mg |
| Propyl paraben | 0.02 | 40 mg |
| EDTA | 0.05 | 100 mg |
| Sodium hydroxide (10%) | | 9 ml |
| Water, q.s. | | to 200 g |

Numerous variations and modifications of the embodiments described above may be effected without departing from the spirit and scope of the novel features of the invention. No limitations with respect to the specific embodiments illustrated herein are intended or should be inferred.

We claim:

1. An aqueous nitroimidazole composition comprising a nitroimidazole selected from the group consisting of metronidazole, tinidazole, and a combination thereof, the composition including at least 1 percent by weight metronidazole and a metronidazole crystallization-inhibiting amount of at least one organic acid which is an organic polybasic acid;

the composition being free from organic co-solvents, water-soluble vitamins, and cyclodextrins; and free from metronidazole crystals at an ambient temperature of about 20° C.

2. The composition of claim 1 wherein the composition further includes at least 0.5 percent by weight of tinidazole.

3. The composition of claim 1 wherein the at least one organic polybasic acid is present in the composition in a molar amount at least equal to the molar amount of nitroimidazole dissolved in the composition.

4. The composition of claim 1 wherein the organic polybasic acid comprises citric acid.

5. The composition of claim 1 wherein the organic polybasic acid comprises a polyacrylic acid.

6. The composition of claim 1 further comprising a thickening agent.

7. The composition of claim 6 wherein the thickening agent comprises a hydroxypropyl methylcellulose.

8. The composition of claim 6, wherein the thickening agent is a polyacrylic acid.

9. The composition of claim 1 wherein the composition comprises at least 1.2 percent by weight of metronidazole.

10. The composition of claim 9 wherein the polybasic acid is present in the composition at a concentration in the range of about 50 to about 150 mole percent based on the molar amount of metronidazole dissolved in the composition.

11. The composition of claim 9 further comprising a thickening agent.

12. The composition of claim 1 wherein the composition comprises at least 0.55 percent by weight of tinidazole.

13. The composition of claim 12 wherein the polybasic acid is present in the composition at a concentration in the range of about 50 to about 150 mole percent based on the molar amount of tinidazole dissolved in the composition.

14. The composition of claim 12 further comprising a thickening agent.

15. A aqueous nitroimidazole gel composition comprising a nitroimidazole selected from the group consisting of metronidazole, tinidazole, and a combination thereof, the composition including at least 1 percent by weight metronidazole; a metronidazole crystallization-inhibiting amount of at least one polybasic organic acid, and a thickening agent in an amount sufficient to gel the composition, said composition being free from nitroimidazole crystals at an ambient temperature of about 20° C.

16. The composition of claim 15 wherein the thickening agent comprises a hydroxypropyl methylcellulose.

17. The composition of claim 15 wherein the thickening agent comprises a polyacrylic acid.

18. The composition of claim 15 wherein the at least one organic acid and the thickening agent each comprise a polyacrylic acid.

19. The composition of claim 15 further comprising a polyol.

20. The composition of claim 19 wherein the polyol comprises propylene glycol.

21. A method for preparing a composition comprising metronidazole at a concentration of at least 1 percent by weight free from organic co-solvents, water-soluble vitamins, and cyclodextrins, and free from metronidazole crystals at an ambient temperature of about 20° C., the method comprising dissolving said metronidazole together with tinidazole if present in an aqueous solution containing a nitroimidazole crystallization-inhibiting amount of at least one polybasic organic acid.

22. The method of claim 21 wherein the composition comprises at least 0.5 percent by weight of tinidazole.

23. The method of claim 21 wherein the polybasic acid is present in the composition at a concentration in the range of about 50 to about 150 mole percent based on the moles of nitroimidazole dissolved in the composition.

24. The method of claim 21 wherein the at least one polybasic organic acid comprises citric acid.

25. The method of claim 21 wherein the at least one polybasic organic acid comprises a polyacrylic acid.

26. An article of manufacture for treating microbial infections comprising packaging material and a composition of claim 15 in a sealed container within the packaging material; the container bearing a label that includes written indicia describing the contents of the container.

27. An article of manufacture for treating microbial infections comprising packaging material and a composition of claim 1 in a sealed container within the packaging material; the container bearing a label that includes written indicia describing the contents of the container.

* * * * *